(12) United States Patent
Ganesh et al.

(10) Patent No.: US 11,070,507 B2
(45) Date of Patent: *Jul. 20, 2021

(54) ENABLING WEARABLES TO COGNITIVELY ALTER NOTIFICATIONS AND IMPROVE SLEEP CYCLES

(71) Applicant: INTERNATIONAL BUSINESS MACHINES CORPORATION, Armonk, NY (US)

(72) Inventors: Bharath Ganesh, Bangalore (IN); Dhandapani Shanmugam, Bangalore (IN); Tuhin Sharma, Bangalore (IN); Jothi Subramani, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/797,232

(22) Filed: Feb. 21, 2020

(65) Prior Publication Data
US 2020/0195599 A1   Jun. 18, 2020

Related U.S. Application Data

(63) Continuation of application No. 16/414,147, filed on May 16, 2019, now Pat. No. 10,616,167, which is a
(Continued)

(51) Int. Cl.
*H04L 12/58*   (2006.01)
*G06F 3/01*   (2006.01)
(Continued)

(52) U.S. Cl.
CPC .......... *H04L 51/24* (2013.01); *A61B 5/4812* (2013.01); *G06F 1/163* (2013.01); *G06Q 10/10* (2013.01);
(Continued)

(58) Field of Classification Search
CPC ......... H04L 51/02; H04L 51/16; H04L 51/24; H04L 51/26; H04L 67/12; H04L 67/125;
(Continued)

(56) References Cited

U.S. PATENT DOCUMENTS 3,884,218 A   5/1975 Monroe
8,233,943 B1 *  7/2012 Othmer ............. H04M 1/72563
455/567
(Continued)

FOREIGN PATENT DOCUMENTS

WO   2017126194 A1   7/2017

OTHER PUBLICATIONS

Harvard Medical School, "Natural Patterns of Sleep", Healthy Sleep, A resource from the Division of Sleep Medicine at Harvard Medical School, Produced in partnership with WGBH Educational Foundation, http://healthysleep.med.harvard.edu/healthy/science/what/sleep-patterns-rem-nrem, last reviewed on Dec. 18, 2007, accessed on Oct. 4, 2017, p. 1-3.
(Continued)

*Primary Examiner* — Ruolei Zong
(74) *Attorney, Agent, or Firm* — Michael O'Keefe

(57) ABSTRACT

A method, computer system, and computer program product for cognitively adjusting a notification alert delivery time are provided. The embodiment may include receiving a message notification from a sender. The embodiment may also include determining an importance of the received message notification based on a plurality of notification attributes and a plurality of person attributes that are each associated with the received message notification. The embodiment may further include, in response to determining to alert a user of the received message notification based on the determined importance, identifying a current user sleep stage. The embodiment may also include, in response to determining
(Continued)

the current user sleep stage will minimally impact the user, transmitting the received message notification to a user device.

17 Claims, 6 Drawing Sheets

Related U.S. Application Data continuation of application No. 15/788,110, filed on Oct. 19, 2017, now Pat. No. 10,616,165.

(51) Int. Cl.
| | | |
|---|---|---|
| *G06F 1/16* | (2006.01) | |
| *H04W 68/00* | (2009.01) | |
| *A61B 5/00* | (2006.01) | |
| *G06Q 10/10* | (2012.01) | |
| *H04W 68/02* | (2009.01) | |
| *H04L 29/08* | (2006.01) | |
| *H04M 1/72436* | (2021.01) | |
| *H04M 1/72454* | (2021.01) | |

(52) U.S. Cl.
CPC ........... *G06Q 10/107* (2013.01); *H04L 51/26* (2013.01); *H04W 68/005* (2013.01); *H04L 51/16* (2013.01); *H04L 67/12* (2013.01); *H04M 1/72436* (2021.01); *H04M 1/72454* (2021.01); *H04M 2242/26* (2013.01); *H04W 68/02* (2013.01)

(58) Field of Classification Search
CPC .............. H04L 67/22; H04M 1/72569; H04M 1/72566; H04M 1/72527; H04M 1/72552; H04M 2242/26; H04W 68/005; H04W 68/02; A61B 5/4812; G06F 1/163
USPC .......................................................... 709/206
See application file for complete search history.

(56) References Cited

U.S. PATENT DOCUMENTS

| | | | |
|---|---|---|---|
| 9,019,106 | B2 | 4/2015 | Alameh |
| 2005/0190065 | A1 | 9/2005 | Ronnholm |
| 2010/0088378 | A1* | 4/2010 | Asawa ................... G06F 16/907 709/206 |
| 2013/0138746 | A1* | 5/2013 | Tardelli ............... H04L 67/1095 709/206 |
| 2014/0221850 | A1 | 8/2014 | Farringdon |
| 2015/0106467 | A1 | 4/2015 | Robarts |
| 2016/0192322 | A1* | 6/2016 | Eramian ................. H04W 4/12 455/466 |
| 2016/0198319 | A1* | 7/2016 | Huang ................... G06F 1/1694 455/412.2 |
| 2016/0275457 | A1 | 9/2016 | Dhillon |
| 2016/0373573 | A1* | 12/2016 | Bivens .................... H04M 3/02 |
| 2018/0315294 | A1* | 11/2018 | Takano ................ A61B 5/4809 |
| 2019/0124032 | A1 | 4/2019 | Ganesh |
| 2019/0273711 | A1 | 9/2019 | Ganesh |

OTHER PUBLICATIONS

Mark Aramli, "5 Stages of Sleep: Your Sleep Cycle Explained", Feb. 2017, BedJet, bedjet.com/blogs/sleep-blog/5-stages-of-sleep (Year: 2017).

Mell et al., "The NIST Definition of Cloud Computing," National Institute of Standards and Technology, Sep. 2011, p. 1-3, Special Publication 800-145.

Takano, English translation of WO-2017126194-A1, Jul. 2017, WIPO (Year: 2017).

IBM: List of IBM Patents or Patent Applications Treated as Related (Appendix P), Mar. 11, 2020, pp. 1-2.

* cited by examiner

US 11,070,507 B2

ENABLING WEARABLES TO COGNITIVELY ALTER NOTIFICATIONS AND IMPROVE SLEEP CYCLES

BACKGROUND

The present invention relates, generally, to the field of computing, and more particularly to wearable technology.

Wearable technology, or wearables, relates to smart electronic devices capable of being worn on a user's body. Many wearables are capable of connecting to a network and, therefore, contribute to the Internet of Things. Typically, wearables incorporate sensors and software that allow for the tracking and exchange of data between entities. Common examples of wearable technology include fitness trackers, sleep trackers, smart watches, hearing devices, navigation tools, media devices, e-textiles, and wearable communicators.

SUMMARY

According to one embodiment, a method, computer system, and computer program product for cognitively adjusting a notification alert delivery time are provided. The embodiment may include receiving a message notification from a sender. The embodiment may also include determining an importance of the received message notification based on a plurality of notification attributes and a plurality of person attributes that are each associated with the received message notification. The embodiment may further include, in response to determining to alert a user of the received message notification based on the determined importance, identifying a current user sleep stage. The embodiment may also include, in response to determining the current user sleep stage will minimally impact the user, transmitting the received message notification to a user device.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
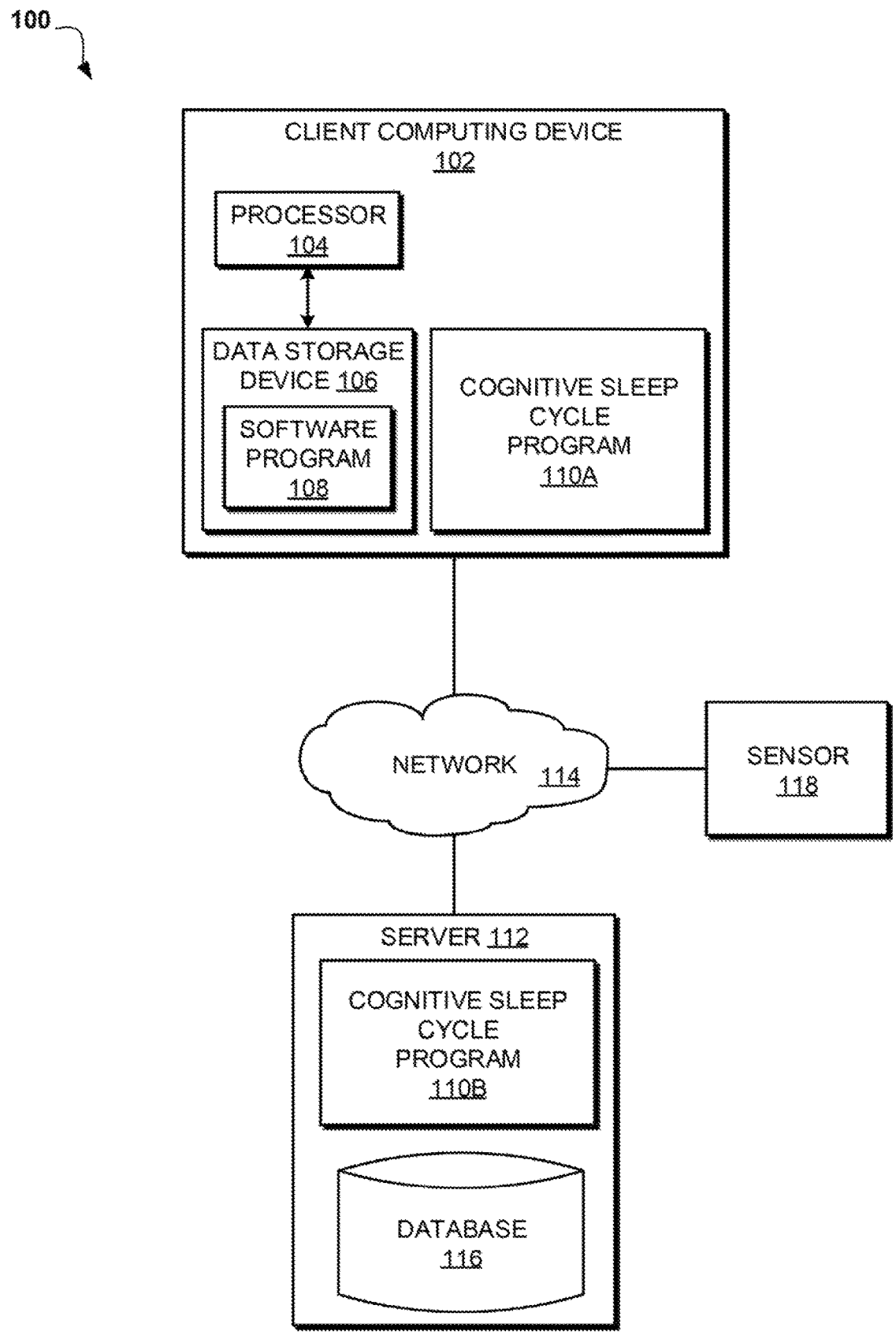
FIG. 1 illustrates an exemplary networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate to the field of computing, and more particularly to wearable technology. The following described exemplary embodiments provide a system, method, and program product to, among other things, alter the time at which a received notification on a wearable device alerts a user so as to minimize the impact caused to the user's sleep quality. Therefore, the present embodiment has the capacity to improve the technical field of wearable technology by enabling wearables to intelligently alter received notifications rather than immediately processing notifications to alert the user.

As previously described, wearable technology, or wearables, relates to smart electronic devices capable of being worn on a user's body. Many wearables are capable of connecting to a network and, therefore, contribute to the Internet of Things. Typically, wearables incorporate sensors and software that allow for the tracking and exchange of data between entities. Common examples of wearable technology include fitness trackers, sleep trackers, smart watches, hearing devices, navigation tools, media devices, e-textiles, and wearable communicators.

With the prevalence of an always-connected mindset in a technological world, uninterrupted sleep may be difficult for some individuals to achieve. Sleep cycles consist of two main sleep types: rapid-eye-movement (REM) sleep; and non-rapid-eye-movement (NREM) sleep. NREM sleep is composed of three distinct stages: N1; N2; and N3. Typically, sleep begins in the NREM sleep stage starting with N1, transitioning to N2, then to N3, and finally to the REM sleep stage. The NREM and REM sleep stages cycle between each other throughout the night. Scientific research has illustrated that the N1 stage of NREM is the lightest sleep stage and the most beneficial sleep stage in which to be woken since the body has not completely shut down. When waking up during the N1 stage of NREM, people may feel more energetic and alert. Some current technologies connect to a user's mobile device to record sleep data and signal the mobile device to wake the user in the lightest phase of sleep within a preconfigured window prior to a desired alarm time.

However, individuals may receive numerous notifications throughout the night, such as incoming short message service (SMS) messages, sports score alerts, phone calls, and emails. Since some notifications may be more important than others to a user, a user may not wish to be woken up when a notification is received. Similarly, since being awoken during certain sleep stages is less impactful on the body, understanding an individual's sleep cycle when a notification is received is dually important. As such, it may be advantageous to, among other things, understand a user's sleep cycle and determine whether a notification is important enough to wake the user during a particular sleep stage.

According to one embodiment, notification attributes may be extracted though semantic analysis, such as notification importance, urgency, involved actors, and event time. An importance score may be calculated based on the notification attributes and associated to an individual notification based on which a revised notification time may be determined. Based on the revised notification time, the user's sleep cycle may be dynamically altered to wake up the user such that minimal impact is caused to the user's sleep quality.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to determine an importance score of a received notification and appropriately transition the user's sleep cycle so as to minimize the impact on the user when an alert is transmitted to the user.

Referring to FIG. 1, an exemplary networked computer environment 100 is depicted, according to at least one embodiment. The networked computer environment 100 may include client computing device 102, a server 112, and a sensor 118 interconnected via a communication network 114. According to at least one implementation, the networked computer environment 100 may include a plurality of client computing devices 102, servers 112, and sensors 118, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a software program 108 and a cognitive sleep cycle program 110A and communicate with the server 112 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 4, the client computing device 102 may include internal components 402a and external components 404a, respectively.

The server computer 112 may be a laptop computer, netbook computer, personal computer (PC), a desktop computer, or any programmable electronic device or any network of programmable electronic devices capable of hosting and running a cognitive sleep cycle program 110B and a database 116 and communicating with the client computing device 102 via the communication network 114, in accordance with embodiments of the invention. As will be discussed with reference to FIG. 4, the server computer 112 may include internal components 402b and external components 404b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

According to the present embodiment, sensor 118 may be a wearable technology device capable of recording user biometric data, such as heartbeat, temperature, and movement, through embedded technology, such as a gyroscope, a thermometer, or a heart rate monitor. The sensor 118 may include a processor, similar to processor 104 in client computing device 102, capable of communicating with the client computing device 102 and the server 112 through the network 114.

The cognitive sleep cycle program 110A, 110B may be a program capable of calculating an importance score of a received notification so that, if the importance score satisfies a threshold, transmission of the notification may be delayed so that the user is in a lighter sleeping stage thereby minimizing the impact on the user's sleep cycle. The cognitive sleep cycle method is explained in further detail below with respect to FIG. 2.

Figure 2:
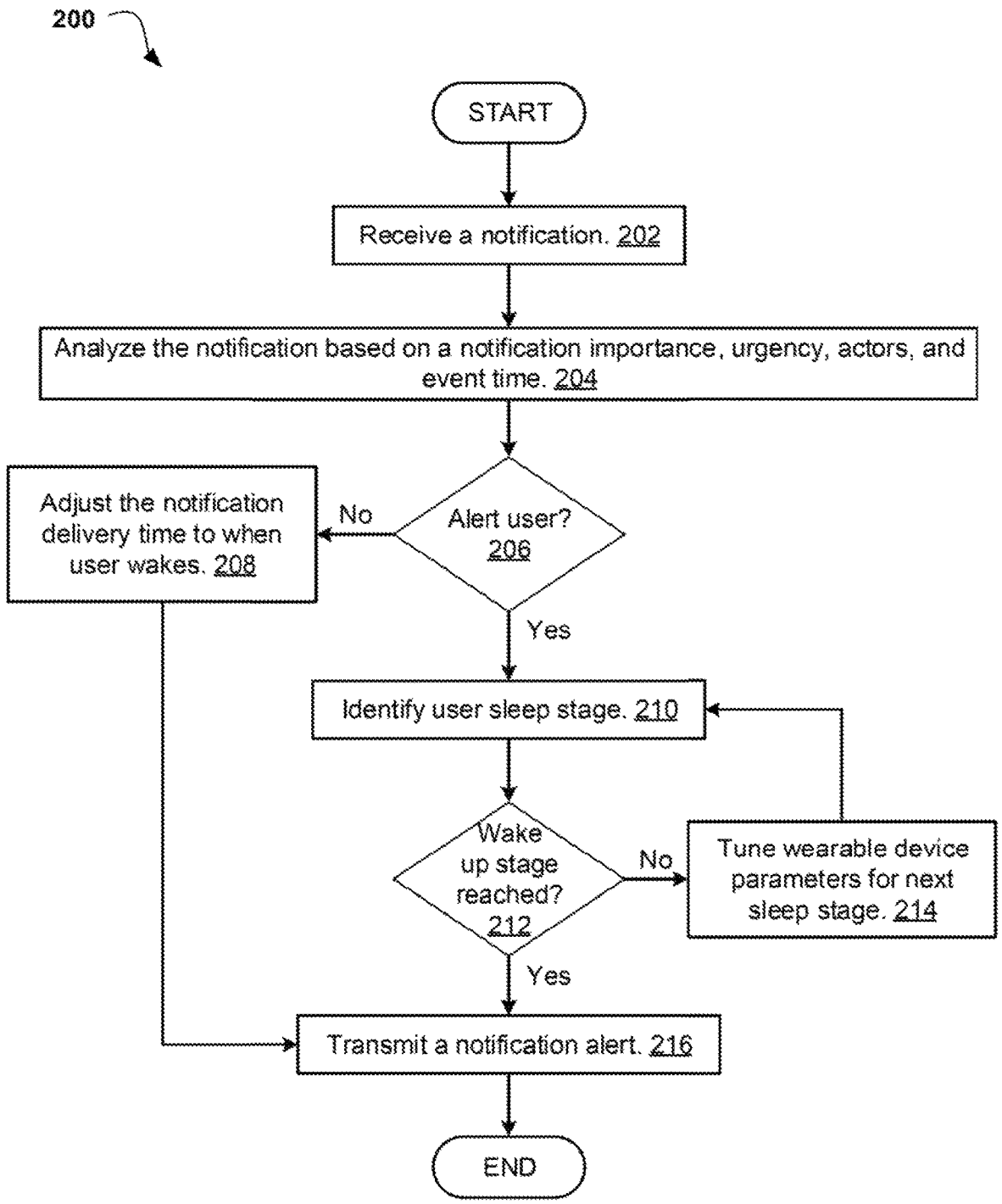
FIG. 2 is an operational flowchart illustrating a cognitive sleep cycle process according to at least one embodiment.

FIG. 2 is an operational flowchart illustrating a cognitive sleep cycle process 200 according to at least one embodiment. At 202, the cognitive sleep cycle program 110A, 110B receives a notification. During the course of a user's sleep cycle, a notification may be received by a user device, such as client computing device 102. For example, the user may be sleeping and receive a text message from a sender with the text, "Are you awake?" The received notification may include attributes specific to the received notification, such as urgency, participating actors, event time, notification message, conversation history, and sender.

Then, at 204, the cognitive sleep cycle program 110A, 110B determines a notification importance based on the notification attributes. The cognitive sleep cycle program 110A, 110B may extract the attribute information within the received notification to calculate a notification importance, which in turn may be used to determine whether the user should be awoken from sleep. As previously described, the attribute information may include urgency, participating actors, event time, message text, conversation history, and sender. In at least one other embodiment, the notification importance may be a categorical value, such as high, medium, or low. In at least one embodiment, the notification importance may be a numerical value that is based on each item of attribute information and is increased or decreased based on user configuration settings for each item. For example, a user may preconfigure the cognitive sleep cycle program 110A, 110B to mark all notifications regarding an event occurring the next day as receiving a high notification importance whereas all notifications relating to an event occurring later than a week from the time the notification is received may be preconfigured to receive a low notification importance.

The urgency of the notification may be a tag that a sending user has placed on the notification. For example, an email may be flagged has high importance by a sending user when transmitting an email to the user. Therefore, the urgency of the notification when the email is received may be tagged as "high".

The participating actors within a received notification may be all individuals taking part in a conversation to which the notification relates. For example, in an email exchange, individuals may be listed in a To: field, a Cc: field, and a Bcc: field. Each individual included in such fields may be considered a participating actor. Similarly, the sender of the notification may be considered a participating actor. The cognitive sleep cycle program 110A, 110B may consider each participating actor when calculating the importance of a notification since the relationship between the user and one or more participating actors may have a proportional connection to the notification importance. For example, if the user is a parent of the notification sender, then the notification importance may be calculated as a high value whereas the notification importance may be a low value for a sender or participating actor that is not related to the user.

Using known text analysis techniques, such as natural language processing, the cognitive sleep cycle program 110A, 110B may evaluate the message content of the notification. For example, a message with the text "I need your help! Are you there?" may be tagged as high importance since the message contains text indicating an immediate response is needed. Conversely, a message with the text "How are you doing?" may be tagged as low importance since the message contains text not requiring an immediate response.

In an example embodiment, the user and a coworker may be in a conversation between 9 P.M. and 11 P.M. discussing the next day's schedule and possible actions. Shortly before falling asleep, the user may reschedule a meeting between the user and the coworker and sends a short message to convey the meeting change. The coworker may receive the message 40 minutes later once the user has gone to sleep and may be on the verge of entering a deep sleep state. The coworker determines the meeting time change is acceptable and acknowledges the meeting change to the user in a short reply message. In such a situation, the cognitive sleep cycle program 110A, 110B may not notify the user on the arrival of the acknowledged message from the coworker since the acknowledgement may receive a low notification importance due to the user and coworker speaking about meeting times earlier and the user being the participant to schedule the meeting whereas the notification is simply an acknowledgement from the coworker of the rescheduled meeting.

In another example embodiment, the user's son may have departed on a weeklong hiking activity in a remote area several hundred miles away from home. When the user's son reaches the destination at 3:30 A.M. local time, he may send a message to inform the user of his arrival. In such a situation, the cognitive sleep cycle program 110A, 110B may calculate the notification importance as high since the message is being sent by the user's son and the message text is confirming the user's son's safety.

Next, at 206, the cognitive sleep cycle program 110A, 110B determines whether to alert the user. According to one implementation, the cognitive sleep cycle process 200 may continue along the operational flowchart if the user should be alerted. The cognitive sleep cycle program 110A, 110B may determine to alert the user if the determined notification importance exceeds an importance threshold. For example, if the notification importance is determined to be high, the cognitive sleep cycle program 110A, 110B may determine the importance threshold is satisfied. If the cognitive sleep cycle program 110A, 110B determines the user should not be alerted (step 206, "No" branch), the cognitive sleep cycle process 200 may continue to step 208 to adjust the notification delivery time for the next comfortable schedule. If the cognitive sleep cycle program 110A, 110B determines the user should be alerted (step 206, "Yes" branch), the cognitive sleep cycle process 200 may continue to step 210 to identify the current user sleep stage.

Then, at 208, the cognitive sleep cycle program 110A, 110B adjusts the notification delivery time to when user wakes. If the cognitive sleep cycle program 110A, 110B determines that the user should not be alerted of the notification based on the importance threshold not being satisfied, the cognitive sleep cycle program 110A, 110B may modify the notification delivery time to transmit the notification alert when the user wakes up from the current sleep session. When the notification delivery time is adjusted, the cognitive sleep cycle program 110A, 110B may continually monitor the user sleep state through wearable technology to identify when the user has woken up based on physiological and psychological attributes captured by the wearable technology device. For example, if the user is wearing a sleep tracking wristband that tracks heartrate and user movement, the cognitive sleep cycle program 110A, 110B may determine that the user has awoken when data from the sleep tracking wristband is received that indicates the user's heartrate has increased and the user has moved. Therefore, the cognitive sleep cycle program 110A, 110B may then transmit the notification alert to the corresponding wearable technology device or the client computing device 102 to alert the user of the received message. In the previously described scenario involving the user and a coworker, the cognitive sleep cycle program 110A, 110B may not alert the user of the coworker's acknowledgement of the rescheduled meeting based on the importance threshold not being satisfied. Therefore, the cognitive sleep cycle program 110A, 110B may adjust the notification delivery time to alert the user when the user has awoken based on the data received from wearable technology devices.

Next, at 210, the cognitive sleep cycle program 110A, 110B identifies the user sleep stage. As previously described, sleep cycles consist of two main sleep types: REM sleep; and NREM sleep. NREM sleep is composed of three distinct stages: N1; N2; and N3. Typically, sleep begins in the NREM sleep stage starting with N1, transitioning to N2, then to N3, and finally to the REM sleep stage. The NREM and REM sleep stages cycle between each other throughout the night. The ordering and length of each sleep stage may proceed as N1 (1-7 minutes), N2 (10-25 minutes), N3 (20-40 minutes), N2 (5-10 minutes), and REM (20-25 minutes). Therefore, the average length of a full sleep cycle may be between 55-108 minutes. Using biometric data, such as heartrate, and movement data received from a wearable technology device, such as a sleep tracker, the cognitive sleep cycle program 110A, 110B may be able to determine when a user has fallen asleep, and the current user sleep stage may be determined based on the estimated length of each sleep stage. For example, if a wearable technology device determines the user fell asleep 15 minutes ago, the cognitive sleep cycle program 110A, 110B may determine the user is in the N2 sleep stage. In at least one embodiment, the cognitive sleep cycle program 110A, 110B may use machine learning, such as a regression model or deep learning, to more accurately estimate the sleep stage length for a user.

Then, at 212, the cognitive sleep cycle program 110A, 110B determines whether a wake up stage has been reached. According to one implementation, the cognitive sleep cycle process 200 may continue along the operational flowchart a wake up stage has been reached. A wake up sleep stage may be a stage of the user sleep cycle within which the user may experience minimal affects from being woken up. The cognitive sleep cycle program 110A, 110B may determine whether a wake up stage has been reached based on the identified sleep stage in step 210. If the cognitive sleep cycle program 110A, 110B determines the user has not reached a wake up sleep stage (step 212, "No" branch), the cognitive sleep cycle process 200 may continue to step 214 to tune wearable device parameters for the next sleep stage. If the cognitive sleep cycle program 110A, 110B determines the user has reached a wake up sleep stage (step 212, "Yes" branch), the cognitive sleep cycle process 200 may continue to step 216 to transmit the notification alert.

Next, at 214, the cognitive sleep cycle program 110A, 110B tunes wearable device parameters for the next sleep stage. In order to wake the user during a sleep stage in which the user will be minimally affected, the cognitive sleep cycle program 110A, 110B may calculate the minimum amount of time left in a user's sleep cycle (T) as the sum of the elapsed time in each previously completed sleep stage ($t_{prev}$) 1, the total amount of time elapsed in the current sleep stage (n), and the minimum allowable notification time delay (ANTD) of the current and remaining sleep stages ($ANTD_{min}$). Therefore, the minimum amount of time a user's sleep cycle may be when a user is currently progressing through a sleep cycle may be calculated as:

$$T = ANTD_{min} + n + t_{prev}$$

In the earlier example where the user received a message from the user's son, the N1 sleep stage may have lasted 7 minutes and 21 minutes may have elapsed in the first N2 sleep stage when the user receives a message of which the cognitive sleep cycle program 110A, 110B determines the user should be alerted. The cognitive sleep cycle program 110A, 110B may calculate the time spent in all previous stages ($t_{prev}$) as 7 minutes since the user has only completed the N1 stage. The time remaining in the current stage (n) may be calculated as 4 minutes. Finally, the minimum allowable notification time delay ($ANTD_{min}$) may be calculated as 49 minutes ($N2_{remaining} + N3 + N2 + REM = 4 + 20 + 5 + 20 = 49$) since there are 4 minutes remaining in the first N2 stage, a minimum of 20 minutes spent in the N3 stage, a minimum of 5 minutes in the second N2 stage, and a minimum of 20 minutes in the REM stage. Therefore, T may be calculated as 77 minutes ($ANTD_{min} + n + t_{prev} = 49 + 21 + 4 = 77$ minutes) which may be distributed among all 5 stages as N1=7 minutes, N2=25 minutes, N3=20 minutes, N2=5 minutes, and REM=20 minutes.

Since the user has already completed the N1 stage and 21 minutes of the first N2 stage, the cognitive sleep cycle program 110A, 110B may optimize the sleep time to awaken the user by calculating the length of a health sleep cycle as:

$$T = m\left(\frac{a+b+1}{2} + ct\right) \text{ where } \frac{a-b+1}{2} \le ct \le \frac{b-a+1}{2}$$

is the cycle threshold for regulating the sleeping cycle duration, $((a+b)/2)+ct$ is the cycle duration, and m is an integer representing the number of sleeping cycles. This equation may have at least one integer solution for m if $b \ge 2a-1$. In the example situation, where a=55 and b=108, the equation may appear as:

$$T = m\left(\frac{55+108+1}{2} + ct\right)$$
$$T = m(82 + ct)$$

where $-27 \le ct \le 27$, $(82+ct)$ is the cycle duration and m is the number of cycles.

The mean duration of the stages for a particular healthy sleeping cycle may have a ratio of:

$$N1:N2:N3:N2:REM = 4:17.5:30:7.5:22.5$$

In the example situation, the duration for each stage for a particular sleeping cycle of X minutes may be as follows:

$$N1 = \frac{4}{4+17.5+30+7.5+22.5} \times X = \frac{4}{81.5}X$$

$$N2 = \frac{17.5}{4+17.5+30+7.5+22.5} \times X = \frac{17.5}{81.5}X$$

$$N3 = \frac{30}{4+17.5+30+7.5+22.5} \times X = \frac{30}{81.5}X$$

$$N2 = \frac{7.5}{4+17.5+30+7.5+22.5} \times X = \frac{7.5}{81.5}X$$

$$REM = \frac{22.5}{4+17.5+30+7.5+22.5} \times X = \frac{22.5}{81.5}X$$

Therefore, if the user wishes to plan T minutes for sleeping, then the duration of each stage in every m number of sleeping cycles of (82+ct) minutes may be as follows:

$$N1 = \frac{4}{81.5}(82 + ct)$$

$$N2 = \frac{17.5}{81.5}(82 + ct)$$

$$N3 = \frac{30}{81.5}(82 + ct)$$

$$N2 = \frac{7.5}{81.5}(82 + ct)$$

$$REM = \frac{22.5}{81.5}(82 + ct)$$

Then, at 216, the cognitive sleep cycle program 110A, 110B transmits an alert to the wearable device. Once the user has reached a sleep stage in which the user may experience minimal affects from being awoken by receiving the notification alert, the cognitive sleep cycle program 110A, 110B may transmit the notification alert to a device, such as a wearable technology device or client computing device 102, to awaken the user. For example, when the user has completed the REM stage of the user's sleep cycle, the cognitive sleep cycle program 110A, 110B may transmit the notification alert that the user's son has safely arrived at his travel destination.

Figure 3:
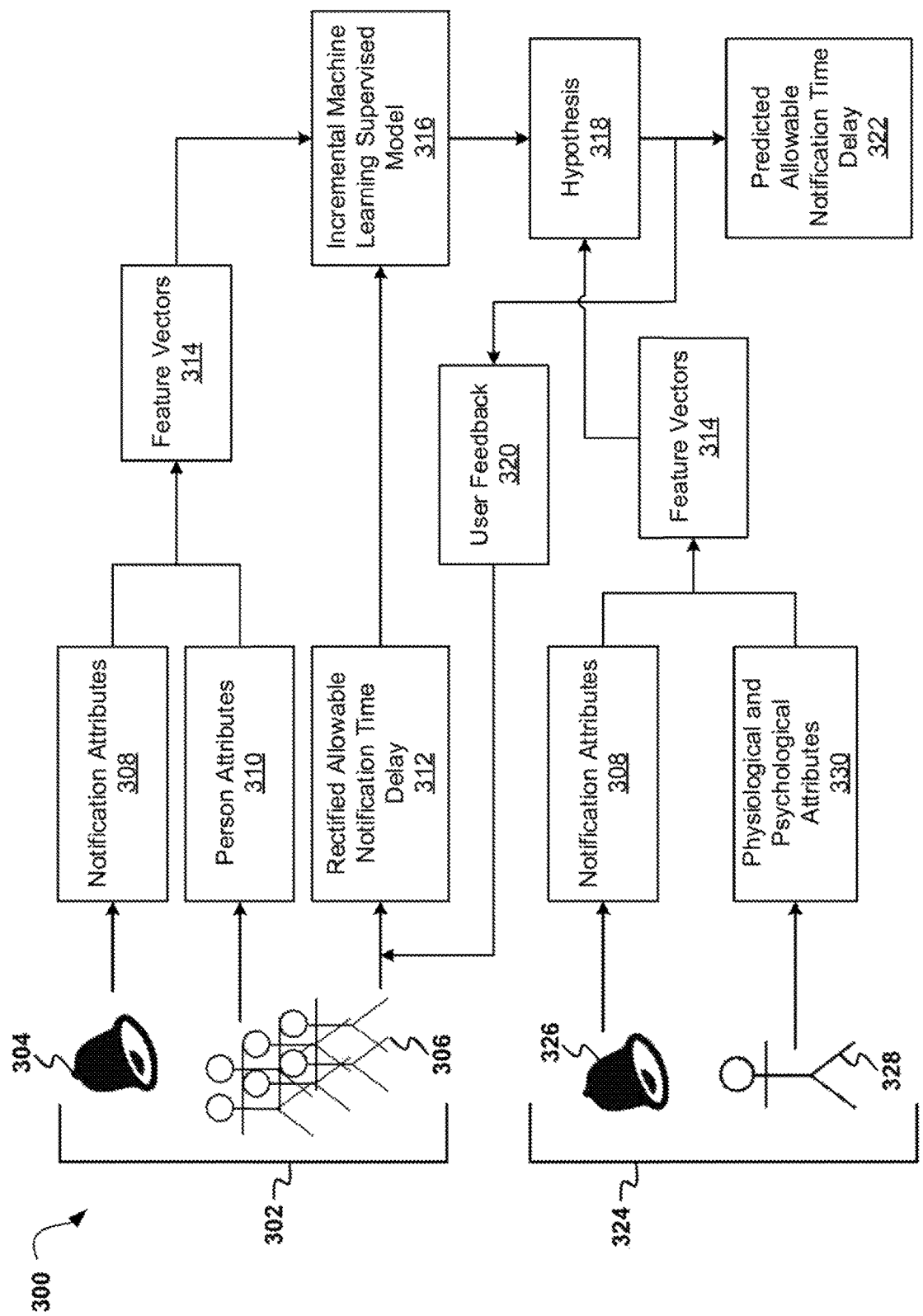
FIG. 3 is an allowable notification time delay calculation block diagram according to at least one embodiment.

Referring now to FIG. 3, an allowable notification time delay calculation block diagram 300 is depicted according to at least one embodiment. The cognitive sleep cycle program 110A, 110B may conduct a training phase 302 and a real-time prediction phase 324. In the training phase 302, the cognitive sleep cycle program 110A, 110B may receive notifications 304 from individuals 306. Each received notification 304 may have accompanying notification attributes 308 and each individual may have associated person attributes 310 that describe the individual, such as name, relationship to user, time of day, upcoming calendar schedule, sleep stage, and location. As previously described, the notification attributes 308 may be extracted from each received notification and may include importance, urgency, actors, event time, and sender. The person attributes 310 may be obtained from an activity tracker or mobile device, such as client computing device 102. The notification attributes 308 and person attributes 310 may be utilized to generate feature vectors 314.

The cognitive sleep cycle program 110A, 110B may utilize the feature vectors 314 and a rectified allowable notification time delay 312 within an incremental machine learning supervised model 316, such as a regression model or deep learning, that may generate a hypothesis of the predicted allowable notification time delay 322. From the hypothesis 318, the cognitive sleep cycle program 110A, 110B may receive user feedback 320 that in turn can be used to refine the rectified allowable notification time delay 312 to further improve prediction accuracy. Therefore, if a user is not satisfied with the predicted allowable notification time delay 322, the user may feed the rectified/corrected ANTD to the incremental machine learning supervised model 316 again with the user feedback 320 so that the incremental machine learning supervised model 316 may retrain.

During the real-time prediction phase 324, the cognitive sleep cycle program 110A, 110B may receive a notification 326 from a sender 328 that includes notification attributes 308 and physiological and psychological attributes 330, such as heartrate, temperature, and user movement. The notification attributes 308 and physiological and psychological attributes 330 may be utilized to generate the feature vectors 314, which in turn may be used to generate the hypothesis 318 and the predicted allowable notification time delay 322.

It may be appreciated that FIGS. 2 and 3 provide only an illustration of one implementation and do not imply any limitations with regard to how different embodiments may be implemented. Many modifications to the depicted environments may be made based on design and implementation requirements.

Figure 4:
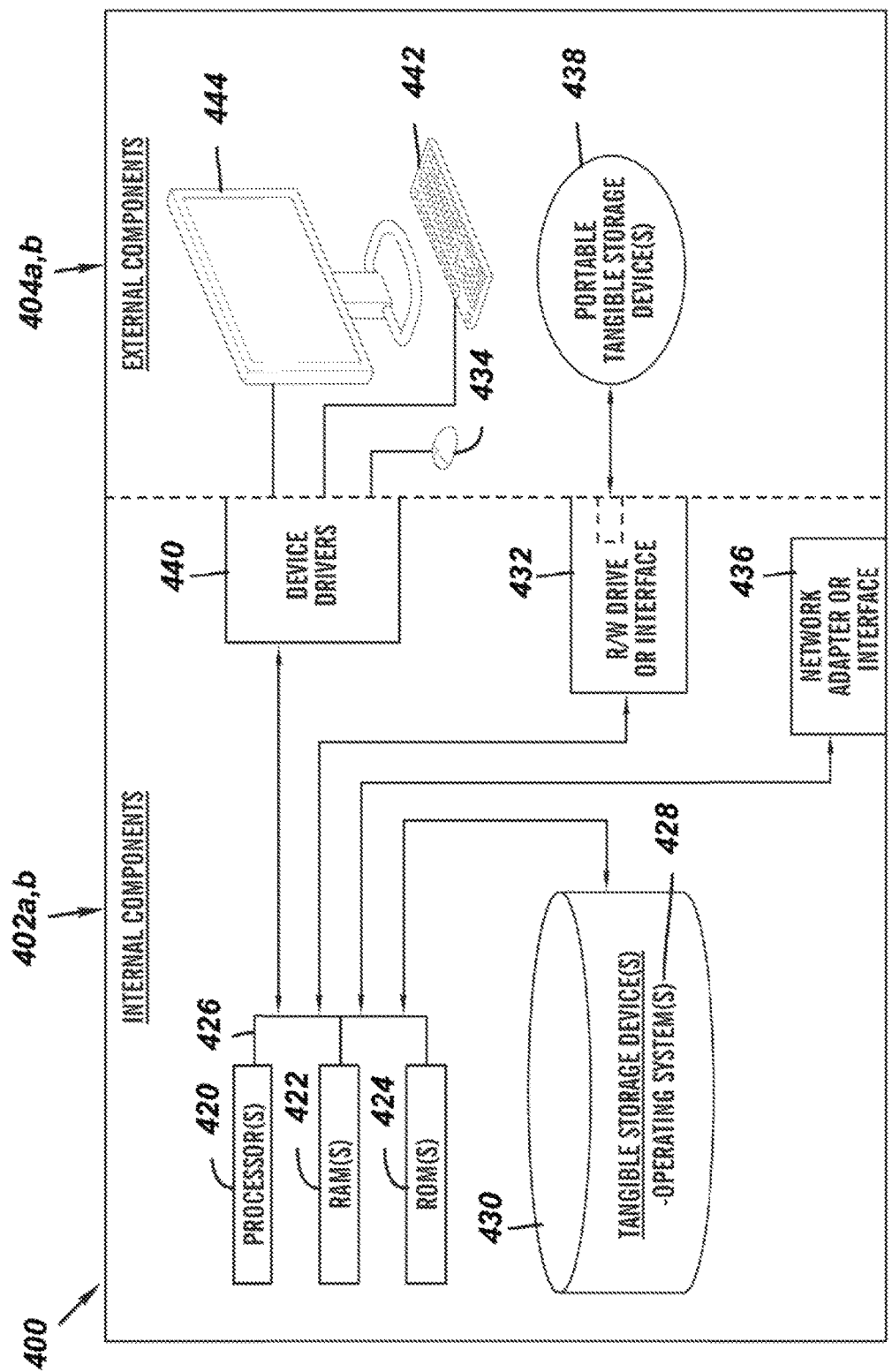
FIG. 4 is a block diagram of internal and external components of computers and servers depicted in FIG. 1 according to at least one embodiment.

FIG. 4 is a block diagram 400 of internal and external components of the client computing device 102 and the server 112 depicted in FIG. 1 in accordance with an embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

The data processing system 402, 404 is representative of any electronic device capable of executing machine-readable program instructions. The data processing system 402, 404 may be representative of a smart phone, a computer system, PDA, or other electronic devices. Examples of computing systems, environments, and/or configurations that may represented by the data processing system 402, 404 include, but are not limited to, personal computer systems, server computer systems, thin clients, thick clients, handheld or laptop devices, multiprocessor systems, microprocessor-based systems, network PCs, minicomputer systems, and distributed cloud computing environments that include any of the above systems or devices.

The client computing device 102 and the server 112 may include respective sets of internal components 402 a,b and external components 404 a,b illustrated in FIG. 4. Each of the sets of internal components 402 include one or more processors 420, one or more computer-readable RAMs 422, and one or more computer-readable ROMs 424 on one or more buses 426, and one or more operating systems 428 and one or more computer-readable tangible storage devices 430. The one or more operating systems 428, the software program 108 and the cognitive sleep cycle program 110A in the client computing device 102 and the cognitive sleep cycle program 110B in the server 112 are stored on one or more of the respective computer-readable tangible storage devices 430 for execution by one or more of the respective processors 420 via one or more of the respective RAMs 422 (which typically include cache memory). In the embodiment illustrated in FIG. 4, each of the computer-readable tangible storage devices 430 is a magnetic disk storage device of an internal hard drive. Alternatively, each of the computer-readable tangible storage devices 430 is a semiconductor storage device such as ROM 424, EPROM, flash memory or any other computer-readable tangible storage device that can store a computer program and digital information.

Each set of internal components 402 a,b also includes a R/W drive or interface 432 to read from and write to one or more portable computer-readable tangible storage devices 438 such as a CD-ROM, DVD, memory stick, magnetic tape, magnetic disk, optical disk or semiconductor storage device. A software program, such as the cognitive sleep cycle program 110A, 110B, can be stored on one or more of the respective portable computer-readable tangible storage devices 438, read via the respective R/W drive or interface 432, and loaded into the respective hard drive 430.

Each set of internal components 402 a,b also includes network adapters or interfaces 436 such as a TCP/IP adapter cards, wireless Wi-Fi interface cards, or 3G or 4G wireless interface cards or other wired or wireless communication links. The software program 108 and the cognitive sleep cycle program 110A in the client computing device 102 and the cognitive sleep cycle program 110B in the server 112 can be downloaded to the client computing device 102 and the server 112 from an external computer via a network (for example, the Internet, a local area network or other, wide area network) and respective network adapters or interfaces 436. From the network adapters or interfaces 436, the software program 108 and the cognitive sleep cycle program 110A in the client computing device 102 and the cognitive sleep cycle program 110B in the server 112 are loaded into the respective hard drive 430. The network may comprise copper wires, optical fibers, wireless transmission, routers, firewalls, switches, gateway computers and/or edge servers.

Each of the sets of external components 404 a,b can include a computer display monitor 444, a keyboard 442, and a computer mouse 434. External components 404 a,b can also include touch screens, virtual keyboards, touch pads, pointing devices, and other human interface devices. Each of the sets of internal components 402 a,b also includes device drivers 440 to interface to computer display monitor 444, keyboard 442, and computer mouse 434. The device drivers 440, R/W drive or interface 432, and network adapter or interface 436 comprise hardware and software (stored in storage device 430 and/or ROM 424).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
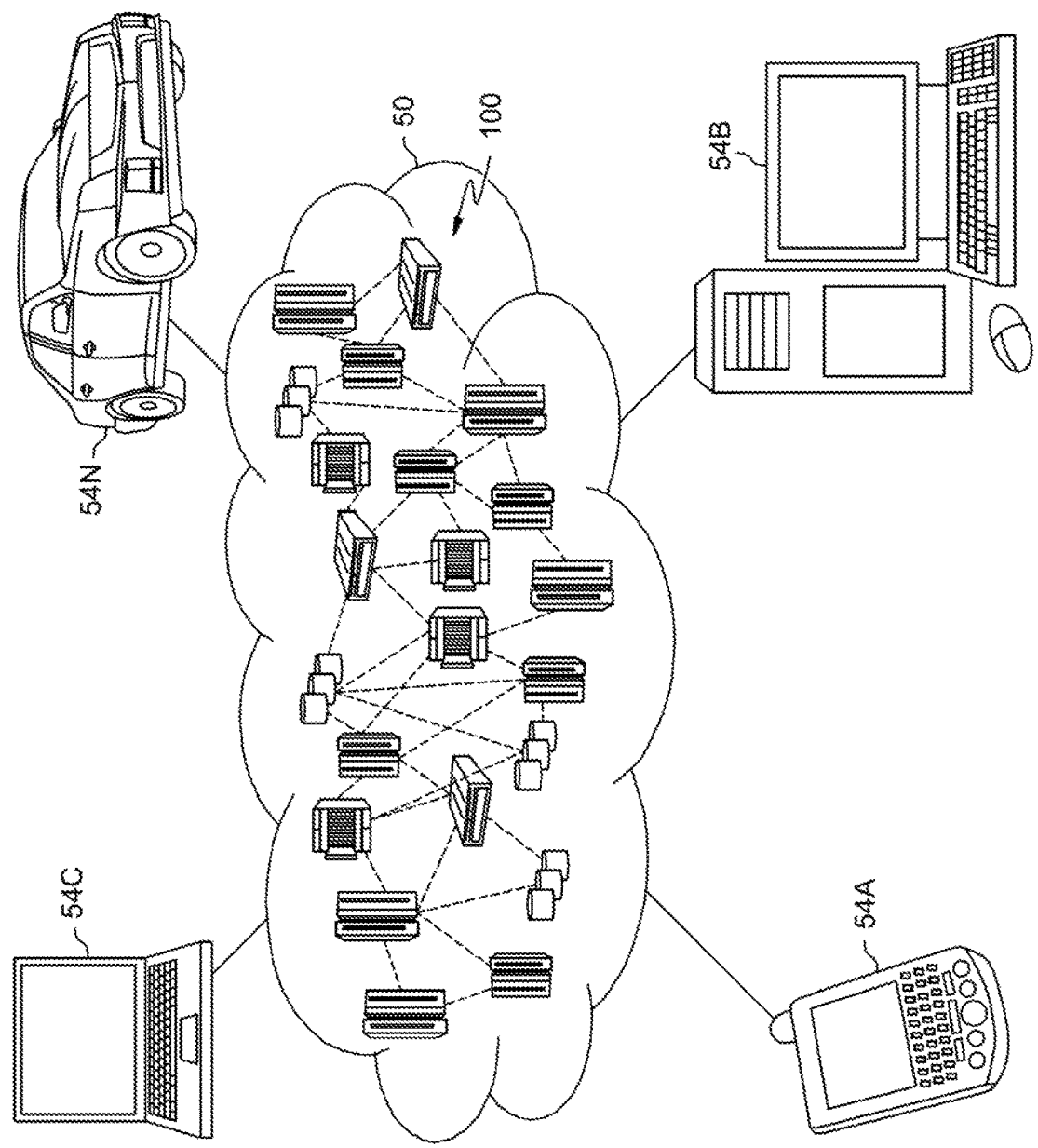
FIG. 5 depicts a cloud computing environment according to an embodiment of the present invention.

Referring now to FIG. 5, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 100 and cloud computing environment 50 can communicate with any type of computerized device over any type of network and/or network addressable connection (e.g., using a web browser).

Figure 6:
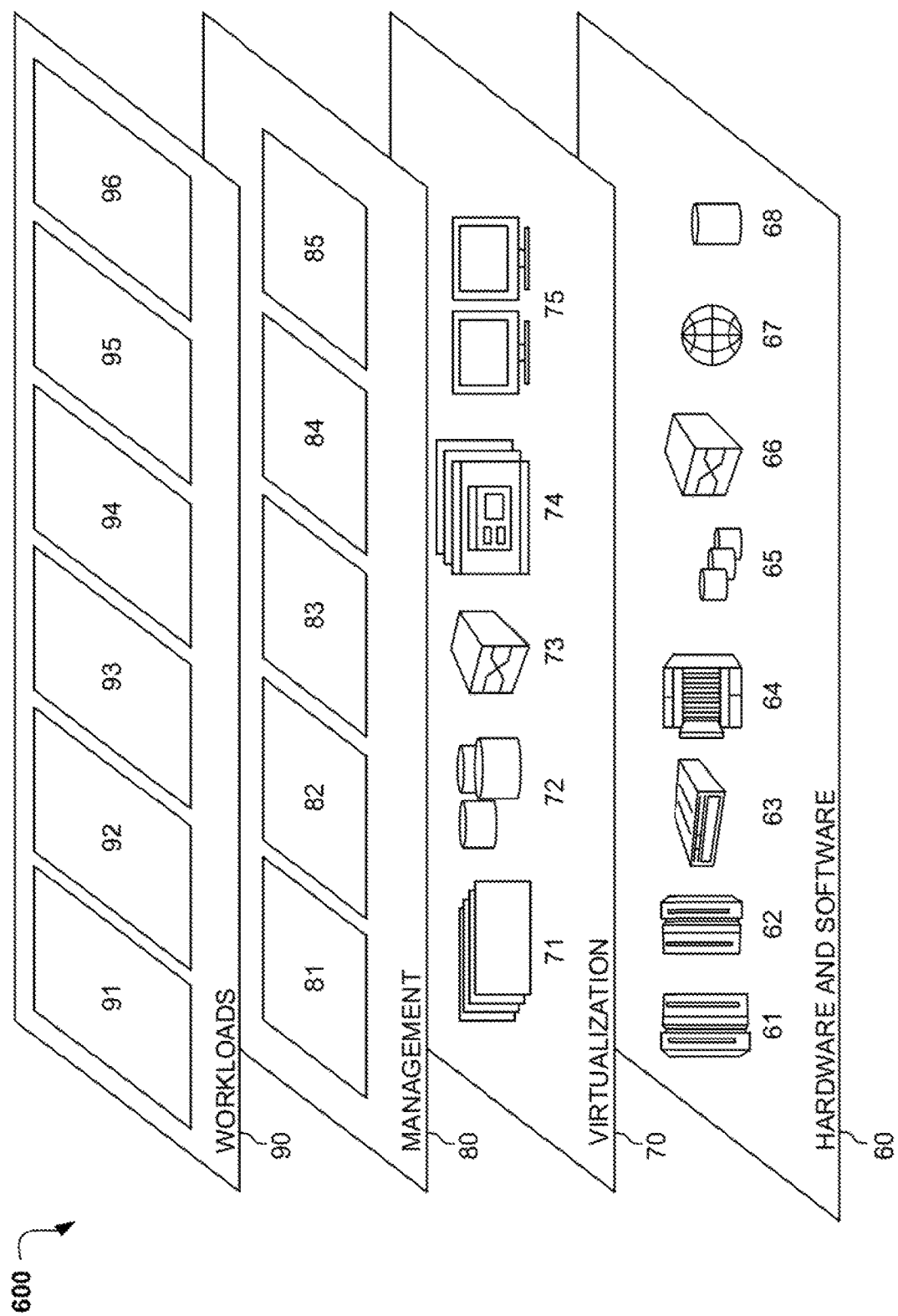
FIG. 6 depicts abstraction model layers according to an embodiment of the present invention.

Referring now to FIG. 6, a set of functional abstraction layers 600 provided by cloud computing environment 50 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and cognitive sleep cycle alteration 96. Cognitive sleep cycle alteration 96 may relate to analyzing characteristics of a received notification to determine a notification importance and, based on the notification importance satisfying a threshold, appropriately delaying the notification alert time so the user sleep cycle is minimally impacted when receiving the received notification.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for cognitively adjusting a notification alert delivery time, the method comprising:
    determining an importance of the received message notification based on a plurality of notification attributes and a plurality of person attributes that are each associated with the received message notification;
    in response to determining to alert a user of the received message notification based on the determined importance, identifying a current user sleep stage; and
    in response to determining the current user sleep stage will not minimally impact the user, tuning one or more wearable technology device parameters for a next sleep stage, wherein tuning the one or more wearable technology device parameters for a next sleep stage further comprises:
        calculating a minimum amount of time left in a user sleep cycle, wherein the minimum amount of time left in the user sleep cycle is calculated as $T=ANTD_{min}+n+t_{prev}$, and wherein T is the time left in the user sleep cycle, $ANTD_{min}$ is a minimum allowable notification time delay of the current and remaining sleep stages, n is a total amount of time elapsed in the current sleep stage, and $t_{prev}$ is a sum of an elapsed time in each previously completed sleep stage.

2. The method of claim 1, wherein the plurality of notification attributes are selected from a group consisting of a message urgency, one or more participating actors, an event time, a plurality of message text, a conversation history, and the sender.

3. The method of claim 1, further comprising:
    in response to determining to not alert the user based on the determined importance, adjusting the notification delivery time to when the user wakes.

4. The method of claim 1, wherein tuning the one or more wearable technology device parameters for a next sleep stage further comprises:
    modifying the notification delivery time based on the calculated minimum amount of time left in the user sleep cycle.

5. The method of claim 4, wherein the minimum amount of time left in the user sleep cycle is calculated as a sum of an elapsed time in each previously completed sleep stage, a total amount of time elapsed in the current user sleep stage and a minimum allowable notification time delay of the current user sleep stage and one or more remaining sleep stages in the user sleep cycle.

6. The method of claim 1, wherein the plurality of person attributes are selected from a group consisting of a sender name, a sender relationship to the user, a time of day, an upcoming calendar schedule, a user sleep stage, a user location, and a sender location.

7. A computer system for cognitively adjusting a notification alert delivery time, the computer system comprising:
    one or more processors, one or more computer-readable memories, one or more computer-readable tangible storage media, and program instructions stored on at least one of the one or more tangible storage media for execution by at least one of the one or more processors via at least one of the one or more memories, wherein the computer system is capable of performing a method comprising:
    determining an importance of the received message notification based on a plurality of notification attributes and a plurality of person attributes that are each associated with the received message notification;
    in response to determining to alert a user of the received message notification based on the determined importance, identifying a current user sleep stage; and
    in response to determining the current user sleep stage will not minimally impact the user, tuning one or more wearable technology device parameters for a next sleep stage, wherein tuning the one or more wearable technology device parameters for a next sleep stage further comprises:
        calculating a minimum amount of time left in a user sleep cycle, wherein the minimum amount of time left in the user sleep cycle is calculated as $T=ANTD_{min}+n+t_{prev}$, and wherein T is the time left in the user sleep cycle, $ANTD_{min}$ is a minimum allowable notification time delay of the current and remaining sleep stages, n is a total amount of time elapsed in the current sleep stage, and $t_{prev}$ is a sum of an elapsed time in each previously completed sleep stage.

8. The computer system of claim 7, wherein the plurality of notification attributes are selected from a group consisting of a message urgency, one or more participating actors, an event time, a plurality of message text, a conversation history, and the sender.

9. The computer system of claim 7, further comprising:
    in response to determining to not alert the user based on the determined importance, adjusting the notification delivery time to when the user wakes.

10. The computer system of claim 7, wherein tuning the one or more wearable technology device parameters for a next sleep stage further comprises:
    modifying the notification delivery time based on the calculated minimum amount of time left in the user sleep cycle.

11. The computer system of claim 10, wherein the minimum amount of time left in the user sleep cycle is calculated as a sum of an elapsed time in each previously completed sleep stage, a total amount of time elapsed in the current user sleep stage and a minimum allowable notification time delay of the current user sleep stage and one or more remaining sleep stages in the user sleep cycle.

12. The computer system of claim 7, wherein the plurality of person attributes are selected from a group consisting of a sender name, a sender relationship to the user, a time of day, an upcoming calendar schedule, a user sleep stage, a user location, and a sender location.

13. A computer program product for cognitively adjusting a notification alert delivery time, the computer program product comprising:
one or more computer-readable tangible storage media and program instructions stored on at least one of the one or more tangible storage media, the program instructions executable by a processor of a computer to perform a method, the method comprising:
determining an importance of the received message notification based on a plurality of notification attributes and a plurality of person attributes that are each associated with the received message notification;
in response to determining to alert a user of the received message notification based on the determined importance, identifying a current user sleep stage; and
in response to determining the current user sleep stage will not minimally impact the user, tuning one or more wearable technology device parameters for a next sleep stage, wherein tuning the one or more wearable technology device parameters for a next sleep stage further comprises:
calculating a minimum amount of time left in a user sleep cycle, wherein the minimum amount of time left in the user sleep cycle is calculated as $T = ANTD_{min} + n + t_{prev}$, and wherein T is the time left in the user sleep cycle, $ANTD_{min}$ is a minimum allowable notification time delay of the current and remaining sleep stages, n is a total amount of time elapsed in the current sleep stage, and $t_{prev}$ is a sum of an elapsed time in each previously completed sleep stage.

14. The computer program product of claim 13, wherein the plurality of notification attributes are selected from a group consisting of a message urgency, one or more participating actors, an event time, a plurality of message text, a conversation history, and the sender.

15. The computer program product of claim 13, further comprising:
in response to determining to not alert the user based on the determined importance, adjusting the notification delivery time to when the user wakes.

16. The computer program product of claim 13, wherein tuning the one or more wearable technology device parameters for a next sleep stage further comprises:
modifying the notification delivery time based on the calculated minimum amount of time left in the user sleep cycle.

17. The computer program product of claim 16, wherein the minimum amount of time left in the user sleep cycle is calculated as a sum of an elapsed time in each previously completed sleep stage, a total amount of time elapsed in the current user sleep stage and a minimum allowable notification time delay of the current user sleep stage and one or more remaining sleep stages in the user sleep cycle.

* * * * *